United States Patent [19]
Mueller et al.

[11] Patent Number: 5,552,159
[45] Date of Patent: Sep. 3, 1996

[54] SOLID DEPOT DRUG FORM

[75] Inventors: Winfried Mueller, Mannheim; Reinhard Spengler; Sven Grabowski, both of Ludwigshafen; Axel Sanner, Frankenthal, all of Germany

[73] Assignee: BASF Aktiengesellschaft, Ludwigshafen, Germany

[21] Appl. No.: 125,133

[22] Filed: Sep. 23, 1993

Related U.S. Application Data

[62] Division of Ser. No. 979,654, Nov. 20, 1992, abandoned.

[30] Foreign Application Priority Data

Nov. 23, 1991 [DE] Germany .................. 41 38 513.6

[51] Int. Cl.⁶ .................................................. A61K 9/20
[52] U.S. Cl. .................... 424/464; 424/486; 424/488
[58] Field of Search ................................ 424/464, 474, 424/486, 487, 488, 489, 436, DIG. 15; 514/966, 967

[56] References Cited

U.S. PATENT DOCUMENTS

| | | | |
|---|---|---|---|
| 2,987,445 | 6/1961 | Levesque | 424/469 |
| 3,432,592 | 3/1969 | Speiser | 424/468 |
| 4,548,990 | 10/1985 | Mueller et al. | 424/486 |
| 4,647,599 | 3/1987 | Bezzegh et al. | 424/19 |
| 4,708,874 | 11/1987 | De Haan et al. | 424/470 |
| 4,784,858 | 11/1988 | Ventouras | 424/468 |
| 4,801,460 | 1/1989 | Goertz et al. | 424/467 |
| 4,837,032 | 6/1989 | Ortega | 424/469 |
| 4,996,065 | 2/1991 | Van de Walle | 426/72 |

FOREIGN PATENT DOCUMENTS

| | | |
|---|---|---|
| 0142877 | 5/1985 | European Pat. Off. . |
| 0240906 | 10/1987 | European Pat. Off. . |
| 0240904 | 10/1987 | European Pat. Off. . |

OTHER PUBLICATIONS

Rubin "Injection Molding", *Encyclopedia of Polymer Science and Engineering*, vol. 8, pp. 102–138.

*Primary Examiner*—Jeffrey C. Mullis
*Attorney, Agent, or Firm*—Oblon, Spivak, McClelland, Maier & Neustadt, P.C.

[57] ABSTRACT

A solid depot drug form produced by melt extrusion at from 50° to 200° C. and continuous shaping of a mixture of from 0.1 to 70% by weight, based on the finished depot form, of a pharmaceutical active ingredient with a polymer melt of the following composition:

a) at least 6% by weight, based on the complete depot form, of at least one water-insoluble poly(meth) acrylate with a glass transition temperature Tg in the range from −60° to 180° C., b) a water-soluble hydroxyalkylcellulose or hydroxyalkylmethylcellulose with 2 or 3 carbons in the hydroxyalkyl, or an N-vinylpyrrolidone polymer with from 0 to 50% by weight of vinyl acetate or a mixture of the two in the ratio a):b) =5:95 to 95:5, and c) 0–30% by weight, based on the finished depot form, of one or more conventional pharmaceutical auxiliaries.

3 Claims, No Drawings

SOLID DEPOT DRUG FORM

This application is a division of application Ser. No. 07/979,654, filed on Nov. 20, 1992, now abandoned.

The present invention relates to a solid depot drug form which is produced by melt extrusion and shaping and in which the active ingredient is embedded in a mixture of at least one particular water-insoluble and at least one particular water-soluble polymer. The shaping is carried out continuously, preferably by hot-cut pelletization.

U.S. Pat. No. 3,432,592 describes the injection molding of polymer melts containing active ingredients. The polymers used therein are expressly stated to be soluble or at least partly soluble in the digestive tract so that release of the active ingredient is ensured. However, partly soluble tablets of this type are mechanically sensitive so that they may be damaged by the peristalsis in the digestive tract, and uniform release of active ingredient is no longer ensured. Reference is made to only the following soluble polymers: a complex polymer which is composed of an amino diol and of an epoxide and which is not conventional in drugs, and polyvinyl alcohol, which is known to be difficult to process, or a partially hydrolyzed copolymer of vinyl acetate and crotonic acid which is soluble only at elevated pH. This process additionally has the disadvantages of injection molding such as a long time spent at elevated temperature and large material losses owing to the feed channels whose contents must not be reused. In addition, the mold costs are extremely high in relation to the production rate.

The extrusion of melts of water-soluble polymers containing active ingredients is disclosed in EP-A 240 904 and EP-A 240 906. However, it has emerged that the products cannot in many cases be stored for long because the depot effect decreases with time.

It is an object of the present invention to develop a solid depot form which is produced by extrusion and continuous shaping and does not have these disadvantages. The advantage of extrusion over other techniques such as granulation and tabletting is that the technology is simple, solvents are avoided, the number and amount of auxiliaries is minimized, it is possible to prepare fixed solutions, elaborate mixing processes are avoided and, in particular, the possibility of demixing of the components is avoided, in other words the composition of the individual depot forms throughout production is reliably absolutely constant. In addition there are the advantages of a continuous process with high throughput and small material losses.

We have found, surprisingly, that depot forms produced from a mixture containing an active ingredient and at least one water-insoluble and at least one water-soluble polymer by extrusion and continuous shaping by calendering or strip or hot-cut pelletization as claimed in claim 1 are stable to mechanical stress, ie. after the solubles have dissolved out there remains a stable framework of insoluble polymer even when it comprises only 6% by weight of the complete depot form. This makes the release rate independent of the paddle speed in an in vitro test. In addition, they are stable on storage, which was likewise not predictable, there being no reduction in the depot effect with time. The depot forms according to the invention are thus superior to all previously disclosed depot forms produced in a similarly simple way by extrusion and injection molding.

The present invention therefore relates to a solid depot drug form produced by melt extrusion at from 50° to 200° C. and continuous shaping of a mixture of from 0.1 to 70% by weight, based on the finished depot form, of a pharmaceutical active ingredient with a polymer melt of the following composition:

a) at least 6% by weight, based on the complete depot form, of at least one water-insoluble poly(meth)-acrylate with a glass transition temperature Tg in the range from −60° to 180° C., b) a water-soluble hydroxyalkylcellulose or hydroxyalkylmethylcellulose with 2 or 3 carbons in the hydroxyalkyl, or an N-vinylpyrrolidone polymer with from 0 to 50% by weight of vinyl acetate or a mixture of the two in the ratio a):b)=5:95 to 95:5, preferably 15:85 to 85:15, and c) 0–30% by weight, based on the finished depot form, of one or more conventional pharmaceutical auxiliaries.

Examples of solid depot drug forms are tablets, coated tablet cores, pellets, granules and suppositories with delayed release of active ingredient. Powders and capsules are not included.

Pharmaceutical active ingredients mean for the purpose of the invention all substances with a pharmaceutical action and minimal side effects as long as they do not decompose under the processing conditions. The amount of active ingredient per dose unit and the concentration may vary within wide limits depending on the activity and release rate. The only condition to be met is that they suffice to achieve the required effect. Thus, the concentration of active ingredient can be in the range from 0.1 to 70, preferably from 0.5 to 60, % by weight.

Suitable water-insoluble polymers a) are only those which contain no physiologically unacceptable monomers, and do not eliminate any such on extrusion either, and which are sufficiently tough and elastic that the solid depot drug forms produced from them are not damaged in the digestive tract. We have found that these conditions are met in an outstanding manner by water-insoluble polyacrylates and polymethacrylates with glass transition temperatures Tg in the range from −60° to 180° C., preferably from 0° to 150° C. These are, in particular, polyacrylic esters of alcohols with 1 to 8 carbons and polymethacrylic esters of alcohols with 1 to 4 carbons, as well as mixtures thereof, preferably copolymers of acrylates and/or methacrylates of alcohols with 1 to 4 carbons with one another and with from 0 to 20 mol % of acrylates and/or methacrylates which contain a quaternary ammonium group in their $C_1$-$C_4$-alcohol component. The effect of these is that the polymer has a certain swellability which may have beneficial effects on the release of active ingredient. Examples which may be mentioned are copolymers of ethyl acrylate, methyl methacrylate and trimethylammonioethyl methacrylate chloride in the molar ratio from 1:2:0.1 to 1:2:0.2.

The water-soluble polymer component b) is composed of hydroxyalkylcellulose or hydroxyalkylmethyl-cellulose with 2 or 3 carbons in the hydroxyalkyl and with a degree of hydroxyalkylation of from 0.5 to 70 and/or with a degree of methoxylation of from 0 to 35%, or of a vinylpyrrolidone homo- or copolymer with up to 50% by weight of vinyl acetate or a mixture of the two.

"Water-soluble" or "water-insoluble" means that at least 10, preferably at least 20, g or less than 10, preferably less than 1, mg of the polymer dissolve in one liter of water at 20° C.

The ratio of polymers a):b) should be in the range from 5:95 to 95:5, preferably from 10:90 to 90:10, parts by weight. Remarkably, it is possible with 6% of component a) to produce tablets whose external shape remains undamaged (although very porous and virtually only as skeleton) in the digestive tract.

Component c) can be composed of one or more conventional pharmaceutical auxiliaries. Suitable examples are:

extenders and/or lubricants such as silicates or diatomaceous earth, stearic acid or salts thereof with, for example, magnesium or calcium, polyethylene glycols, cellulose derivatives, talc, sucrose, lactose, cereal or corn starch, potato flour, as well as wetting agents, preservatives, redox stabilizers, plasticizers, adsorbents, flavorings (cf., for example, H. Sucker et al., Pharmazeutische Technologie, Thieme-Verlag, Stuttgart 1978).

The mixing of the active ingredient or ingredients with the polymeric binders, with or without other conventional pharmaceutical additives, can take place before or after the melting of the polymeric binder by conventional processes. Mixing is preferably carried out in an extruder, preferably a twin screw extruder or a single screw extruder with mixing section.

The polymeric binder should soften or melt in the complete mixture of all the components in the range from 50 to 180, preferably from 60° to 150° C. so that the material can be extruded. The glass transition temperature of the polymers must therefore always be below 180° C.

The melts are free of solvent. This means that no water and no organic solvent is added.

The shaping is effected by extrusion at from 50° to 180° C., preferably from 60° to 150° C., and subsequent continuous shaping of the still plastic extrudate, eg. to tablets, for example as described in U.S. Pat. No. 4,880,585, by passing the extrudate between two counter-rotating rolls with opposing depressions in their surfaces, whose design determines the shape of the tablets. Strip pelletization is also suitable.

Hot-cut pelletization is preferred. This entails the extrudates being cut by rotating knives immediately after emergence from the die, expediently into pieces whose length is roughly the same as the diameter of the extrudate. These cut-off particles of the melt cool in the stream of air or gas so that the surface is non-tacky before there is contact with other particles or a vessel wall but, on the other hand, the particles are still sufficiently plastic to acquire a spherical shape due to collisions, eg. with the wall of a downstream cyclone. The particles obtained in this straightforward manner are substantially spherical or lenticular and have diameters of from 0.5 to 4, preferably from 0.8 to 2 mm. The preferred smaller particles are primarily suitable for filling capsules.

If required it is also possible to provide the solid drug form with a conventional coating to improve the appearance and/or the taste (coated tablet) or for additional delay of release of active ingredient. For oral tablets with delayed release of active ingredient it may be beneficial for the tablets to be produced by one of the conventional techniques in closed-cell porous form so that they float in the stomach and thus remain there longer.

The invention permits in a simple and environmentally acceptable manner (without solvent) specific adjustment of the depot effects substantially independently of the shape and the size of the drug form. The drug forms according to the invention remain substantially dimensionally stable in the digestive tract so that release of active ingredient takes place virtually exclusively by diffusion. The invention also makes it possible to achieve pH-independent release of active ingredient. The depot effect can also be adjusted extremely strictly even for small depot forms. The variation in release of active ingredient is, because of the great homogeneity of the material in conjunction with the dimensional stability, low and outstandingly reproducible. The kinetics of release of the active ingredient remain surprisingly stable even on storage under extreme climatic conditions (temperature, humidity). It is furthermore surprising that the drug forms according to the invention show virtually no cold flow, in contrast to extruded drug forms which contain no water-insoluble polymer.

EXAMPLES

Example 1

60 parts of theophylline, 10 parts of a copolymer with a K value of 30 and composed of 60% by weight of N-vinylpyrrolidone and 40% by weight of vinyl acetate, 10 parts of hydroxypropylcellulose (Klucel® EF supplied by Aqualon) and 20 parts of a copolymer of ethyl acrylate, methyl methacrylate and trimethylammonioethyl methacrylate chloride (molar ratio 1:2:0.1; Eudragit® RS supplied by Röhm Pharma, Weiterstadt) were mixed and extruded in a twin screw extruder. The extruder sections were at 70, 80, 100 and 120° C., and the die was at 130° C. The resulting extrudate was fed into an embossing calender with 750 mg molds. In the USP XXI no-change test at pH 1.2 and pH 6.8 the release of active ingredient from the tablets was 62% in 8 h, irrespective of the pH and of the paddle speed. The tablets were stable on storage at 50° C. and 30° C./75% relative humidity for at least 1 year.

Example 2

50 parts of theophylline, 30 parts of a copolymer with a K value of 30 and composed of 60% by weight of N-vinylpyrrolidone and 40% by weight of vinyl acetate, and 20 parts of a copolymer of methyl methacrylate and ethyl acrylate (in the ratio 2:1 by weight) were processed under the conditions of Example 1 and calendered with 500 mg molds. The release of active ingredient after 8 h was 68%, irrespective of the pH.

Example 3

50 parts of theophylline, 10 parts of hydroxy-propylcellulose and 30 parts of a copolymer of ethyl acrylate, methyl methacrylate and trimethylammonioethyl methacrylate chloride (molar ratio 1:2:0.1) and 10 parts of a copolymer of ethyl acrylate, methyl methacrylate and trimethylammonioethyl methacrylate chloride (molar ratio 1:2:0.2, Eudragit® RL supplied by Röhm Pharma, Weiterstadt) were mixed and extruded in a twin screw extruder. The extruder sections were at 70, 80, 100 and 120° C. and the die was at 130° C. The extrudates emerging from the 1.0 mm die were cut off (hot cut) by a rotating knife so that substantially spherical particles were obtained after cooling in a stream of air and cyclone separation. 90% of the particles had a diameter of from 1.0 to 1.5 mm. The release of active ingredient reached 60% in 8 h.

Example 4

6 parts of biperiden, 9 parts of a copolymer with a K value of 30 and composed of 60% by weight of N-vinyl-pyrrolidone and 40% by weight of vinyl acetate, 10 parts of hydroxypropylcellulose, and 75 parts of a copolymer of ethyl acrylate, methyl methacrylate and trimethylammonioethyl methacrylate chloride (molar ratio 1:2:0.1) were extruded (70, 80, 100 and 110° C., dies 110° C.) and hot-cut (die diameter 0.8 mm). 95% of the pellets had a diameter of from 0.8 to 1.3 mm. The release of the active ingredient in 8 h was 83%.

Example 5

Pellets were prepared as in the above examples from 20 parts of nifedipine, 62.5 parts of a copolymer with a K value of 30 and composed of 60% by weight of N-vinylpyrrolidone and 40% by weight of vinyl acetate, and 17.5 parts of a copolymer of ethyl acrylate, methyl methacrylate and trimethylammonioethyl methacrylate chloride (molar ratio 1:2:0.1) (sections at 80/100/100/115° C. die at 120° C., die diameter 10 mm). 87% of the particles had a diameter of from 1.25 to 1.8 mm. The release of active ingredient in 8 h was 52%. No nifedipine crystals were detectable either by Debye-Scherrer X-ray measurements or in DSC investigations.

Example 6

40 parts of melperone, 30 parts of a copolymer which had a K value of 30 and was composed of 60% by weight of N-vinylpyrrolidone and 40% by weight of vinyl acetate, and 30 parts of a copolymer of ethyl acrylate, methyl methacrylate and trimethylammonioethyl methacrylate chloride (molar ratio 1:2:0.1) were extruded (sections at 60, 70, 80, 90 and 100° C., die at 120° C.) and calandered with 500 mg molds. In the USP XXI no-change test at pH 1.2 and pH 6.8 the tablets showed a pH-independent release of active ingredient of 85% in 8 h.

Example 7

40 parts of melperone, 12 parts of a copolymer which had a K value of 30 and was composed of 60% by weight of N-vinylpyrrolidone and 40% by weight of vinyl acetate, 8 parts of hydroxypropylcellulose and 40 parts of a copolymer of ethyl acrylate, methyl methacrylate and trimethylammonioethyl methacrylate chloride (molar ratio 1:2:0.1 ) were extruded and hot-cut ( see Example 3, sections at 60, 80, 90 and 110° C., die at 120° C., die diameter 1.0 mm). 95% of the pellets had a diameter of from 1.2 to 1.8 mm. The release of active ingredient in 8 h was 96%.

We claim:

1. A process for the production of a solid depot drug form which comprises melt extruding at from 50° to 200° C. and hot cut pelletizing a mixture of from 0.1 to 70% by weight, based on the finished depot form, of a pharmaceutically active ingredient with a polymer melt of the following composition:

(a) At least 6% by weight, based on the complete depot form, of a extrudable water-insoluble poly(meth)acrylate with a glass transition temperature Tg in the range from −60° to 180° C., and (b) A polymer which is (1') a water-soluble hydroxyalkylcellulose or (1") hydroxyalkylmethylcellulose with 2 or 3 carbons in the hydroxyalky, or (2) an N-vinylpyrrolidone polymer with from 0 to 50% by weight of vinyl acetate or (3) a mixture of b(1') or b(1") and b(2) wherein polymer (b) is present in an amount of 5% to 95% of the weight of (a) and (b), and (c) 0–30% by weight, based on the finished depot form, of one or more conventional pharmaceutical auxiliaries, the said extrudable water-insoluble poly(meth)acrylate having a solubility of less than 10 mg in one liter of water at 20° C.

2. A process according to claim 1, wherein polymer (a) is composed of from 80 to 100 mol % of a copolymer of an acrylate of $C_1$–$C_8$-alcohols and a methacrylate of $C_1$–$C_4$-alcohols and from 0 to 20 mol % of a (meth)acrylate containing quaternary ammonium groups.

3. A process according to claim 1, wherein polymer (a) is composed of a polymer of an acrylate of $C_1$–$C_8$-alcohols or a polymer of a methacrylate of $C_1$–$C_4$-alcohols or of a copolymer of said acrylate or methacrylate with up to 20 mol % of a (meth)acrylate containing quaternary ammonium groups.

\* \* \* \* \*